(12) United States Patent
Kane et al.

(10) Patent No.: US 7,079,254 B2
(45) Date of Patent: Jul. 18, 2006

(54) METHOD AND APPARATUS FOR IMAGING INTERNAL STRUCTURES OF TRANSPARENT AND TRANSLUCENT MATERIALS

(75) Inventors: Daniel J. Kane, Santa Fe, NM (US); Andrei B. Vakhtin, Los Alamos, NM (US); Kristen A. Peterson, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 10/804,804

(22) Filed: Mar. 18, 2004

(65) Prior Publication Data

US 2004/0239946 A1 Dec. 2, 2004

Related U.S. Application Data

(60) Provisional application No. 60/458,111, filed on Mar. 26, 2003.

(51) Int. Cl.
*G01B 9/02* (2006.01)
*G01J 3/45* (2006.01)

(52) U.S. Cl. ..................................... 356/456
(58) Field of Classification Search ........ 356/451–456, 356/479, 497
See application file for complete search history.

(56) References Cited

U.S. PATENT DOCUMENTS

| | | | |
|---|---|---|---|
| 5,166,749 A * | 11/1992 | Curbelo et al. ............. 356/452 |
| 5,321,501 A | 6/1994 | Swanson et al. | |
| 5,459,570 A | 10/1995 | Swanson et al. | |
| 5,539,518 A * | 7/1996 | Bennett ....................... 356/452 |
| 5,565,986 A | 10/1996 | Knuttel | |
| 5,877,856 A | 3/1999 | Fercher | |
| 6,134,003 A | 10/2000 | Tearney et al. | |
| 6,351,307 B1 * | 2/2002 | Erskine ....................... 356/451 |
| 6,377,349 B1 | 4/2002 | Fercher | |
| 6,421,164 B1 | 7/2002 | Tearney et al. | |

OTHER PUBLICATIONS

Fercher, Adolph F., et al., "Measurement of Introocular Distances by Backscattering Spectral Interferometry", *Optics Communications*, vol. 117, (May 15, 1995),43-48.
Hausler, Gerd, et al., ""Coherence Radar" and Spectral Radar"—New Tools for Dermatological Diagnosis, *Journal of Biomedical Optics*, vol. 3, No. 1, (Jan. 1998),21-31.
Leitgeb, Rainer A., et al., "Performance of Fourier Domain vs. Time Domain Optical Coherence Tomography", *Optics Express*, vol. 11, No. 8, (Apr. 21, 2003),889-894.
Leitgeb, Rainer A., et al., "Phase-Shifting Algorithm to Achieve High-Speed Long-Depth-Range Probing by Frequency-Domain Optical Coherence Tomography", *Optics Letters*, vol. 28, No. 22, (Nov. 15, 2003),2201-2203.

(Continued)

*Primary Examiner*—Hwa (Andrew) Lee
*Assistant Examiner*—Patrick Connolly
(74) *Attorney, Agent, or Firm*—Jeffrey D. Myers; Peacock Myers, P.C.

(57) ABSTRACT

An apparatus and method for spectral interferometry comprising providing an interferometer comprising a light source and dithering an element to provide a continuous relative phase shift between target and reference arms of the interferometer.

32 Claims, 9 Drawing Sheets

OTHER PUBLICATIONS

Pennwell Corporation, "Differential Spectral Interferometry May Boost Dynamic Range of OCT", *OptoElectronics World New, Laser Focus World*, (Jan. 2004).

Schmit, Joanna, et al., "Extended Averaging Technique for Derivation of Error-Compensating Algorithms in Phase-Shifting Interferometry", *Applied Optics*, vol. 34, No. 19, (Jul. 1, 1995),3610-3619.

Vakhtin, Andrei B., et al., "Common-Path Interferometer for Frequency-Domain Optical Coherence Tomography", *Applied Optics*, vol. 42, No. 34, Inventors' published paper,(Dec. 1, 2003),6953-6958.

Vakhtin, Andrei B., et al., "Differential Spectral Interferometry: An Imaging Technique for Biomedical Applications", *Optics Letters*, vol. 28, No. 15, Inventors' published paper,(Aug. 1, 2003), 1332-1334.

Van Staveren, Hugo J., et al., "Light Scattering in Intralipid—10% in the Wavelength Range of 400-1100 nm", *Applied Optics*, vol. 30, No. 31, (Nov. 1, 1991),4507-4514.

Wojtkowski, Maciej, et al., "Full Range Complex Spectral Optical Coherence Tomography Technique in Eye Imaging", *Optics Letters*, vol. 27, No. 15, (Aug. 15, 2002), 1415-1417.

Wojtkowski, Maciej, et al., "In Vivo Human Retinal Imaging by Fourier Domain Optical Coherence Tomography", *Journal of Biomedical Optics*, vol. 7, No. 3, (Jul. 2002),457-463.

* cited by examiner

METHOD AND APPARATUS FOR IMAGING INTERNAL STRUCTURES OF TRANSPARENT AND TRANSLUCENT MATERIALS

CROSS-REFERENCE TO RELATED APPLICATIONS

This application claims the benefit of the filing of U.S. Provisional Patent Application Ser. No. 60/458,111, entitled "Method and Apparatus for Imaging Internal Structures of Transparent and Translucent Materials", filed on Mar. 26, 2003, and the specification thereof is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. DMI-0214911 awarded by the U.S. National Science Foundation (NSF).

BACKGROUND OF THE INVENTION

1. Field of the Invention (Technical Field)

The present invention is of differential spectral interferometry (DSI), a novel method for biomedical and materials imaging, which combines the high dynamic range of optical coherence tomography (OCT) with inherently parallel low-bandwidth image acquisition of spectral interferometry (SI). DSI efficiently removes the deleterious DC background inherent in SI measurements while maintaining the parallel nature of SI. The invention is demonstrated for both synthetic and biological samples. Because DSI is mechanically simpler than OCT, while preserving the low bandwidth, parallel nature of SI, it is competitive with OCT for biomedical applications in terms of image quality and acquisition rate.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Optical coherence tomography (OCT) and spectral interferometry (SI) are low coherence optical imaging methods related to each other through the Fourier transform (FT). OCT, which takes measurements in the time domain, provides good dynamic range and image resolution. It has been demonstrated that OCT can be successfully used for subsurface biomedical imaging at nearly video rate. A drawback of OCT is the requirement for a high-speed optical delay line in the reference arm. SI makes measurements in the frequency domain, taking advantage of inherently parallel spectral data acquisition and an optical arrangement without moving parts or high-speed modulation. Recently, Applicants reported on successful use of SI for 3D-imaging in *Xenopus* tadpoles. A. B. Vakhtin, et al., "Differential spectral interferometry: an imaging technique for biomedical applications", *Opt. Lett.* 28,1332 (August 2003); and A. B. Vakhtin, et al. "Common path interferometer for frequency-domain optical coherence tomography," *Appl. Opt.* 42, 6953 (December 2003).

The main drawback of SI is the DC character of the measurements, which results in a relatively low imaging dynamic range. A strong background associated with the spectrum of the light source itself (DC term) and the interfering waves scattered from different surfaces within the sample (autocorrelation terms) are inherently present in SI images. It is the DC and autocorrelation terms that keep the dynamic range of SI far below the theoretical shot-noise limit, thus limiting the usefulness of SI for biomedical imaging. To eliminate these two artifacts of SI, M. Wojtkowski, et al., "Complex spectral OCT in eye imaging", Opt. Lett. 27, 1415 (August 2002), recently suggested an approach that involves complex five-frame phase and amplitude reconstruction. The method improves the signal-to-noise ratio and doubles the depth range by using both positive and negative optical path differences for imaging; however, it requires exceptional stability of the object—$\lambda/10$ within the complex-method data measurement time scale, which is 6–120 s.

A major advantage of the high-speed differential detection of the invention is that it rejects 1/f noise. In the case of 1/f noise, the magnitude of low frequency components is much larger than the magnitude of high frequency components. Thus, when the detection bandwidth allows low frequency components to pass, the noise levels are higher simply because the amplitude of the low frequency components is higher.

Therefore, it is imperative to reject low-frequency components, which is not taught by either U.S. Pat. No. 5,565,986, to knüttel or U.S. Pat. No. 6,377,349, to Fercher. While they do demonstrate that a dither in the reference arm can be added to enhance data collection and reject background terms, they do not teach or suggest that the dither and the differential data collection must be performed at high-speed. In fact, Leitgeb et al. (including Fercher) teach that simply integrating the array detector for a short period of time rejects 1/f noise. R. Leitgeb, et al., *Optics Express*, 11, 889–894 (21 Apr. 2003). They explicitly state that: "Fourier domain systems record one full A-scan in parallel. For short exposure times (<1 ms) also in this case 1/f noise will be neglected." This is incorrect. To first order, a single short exposure passes all frequencies from DC up to approximately the reciprocal of the pulse width. To reject DC and low frequencies, the array must be integrated for a short period time, and the time separation between the shifted interferograms must be short, for it is this time separation—not the integration time—that determines the measurement bandwidth. In other words, synchronous detection as in the present invention must be used.

BRIEF SUMMARY OF THE INVENTION

The present invention is of an apparatus and method for spectral interferometry, comprising: providing an interferometer comprising a light source; and dithering an element to provide a continuous relative phase shift between target and reference arms of the interferometer. In the preferred embodiment, the light source is mode locked. The invention subtracts spectra that differ by the phase shift to create a differential spectral interferogram, then performs a Fourier transform of the differential spectral interferogram, whereby an amplitude of a signal of interest is improved by a factor of approximately two as compared to non-differential spectral interferometry. Both real and imaginary components of a complex interferogram are determined, which substantially removes 1/f noise. The element preferably comprises a piezo translator. Lock-in detection for each of one or more pixels of a detector is preferably employed. The phase shift is preferably approximately $\pi$, the invention substantially rejects 1/f noise, substantially rejects low frequency noise, and substantially reduces detection bandwidth. Synchronous detection is preferably employed, most preferably lock-in detection.

The invention is also of an apparatus and method for spectral interferometry, comprising: providing an interferometer comprising a light source; dithering an element to provide a continuous relative phase shift between target and reference arms of the interferometer; and providing synchronous detection for each of one or more pixels of a detector.

The invention is further of an apparatus and method for spectral interferometry, comprising: providing an interferometer comprising a light source; employing an element to provide a relative phase shift between target and reference arms of the interferometer; and providing synchronous detection for each of one or more pixels of a detector.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Figure 1:
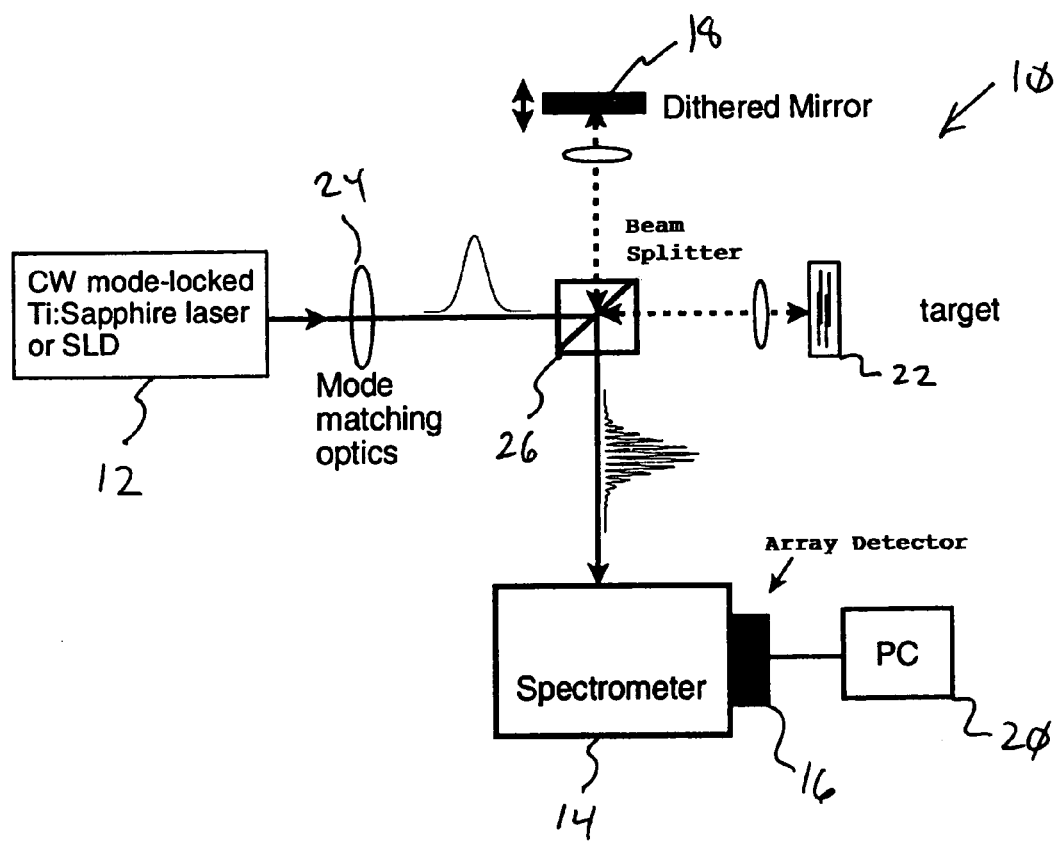
FIG. 1 is the schematic diagram of the preferred DSI instrument according to the invention. The instrument is preferably constructed from the general form of a Michelson interferometer. The sample is in one arm and a dithered mirror is placed in the other arm. The output is spectrally resolved. Detection is synchronous with the dither.

Best Modes for Carrying Out the Invention

The present invention is of a differential spectral interferometry (DSI) method and apparatus which combines the advantages of both OCT and SI. The invention includes a modification of SI that requires only a small $\lambda/2$ dither (n phase shift) of the interferometer's reference path or, equivalently, a $\lambda/4$ or $\pi/2$ phase shift in the reference arm. Although DSI does not distinguish between the positive and negative optical path differences, it eliminates the DC and autocorrelation terms. It is much simpler than a five-frame complex reconstruction method and is not sensitive to the sample instability. A differential spectral interferogram is obtained by subtracting two spectra that differ only by a $\pi$ phase shift in the reference path. A Fourier transform of the differential spectral interferogram produces an image that is free of the background inherent in SI, with the signal of interest increased by a factor of two (compared to SI). As with SI, the spectral data are collected in a parallel way, however the data acquisition can be performed in an AC mode, which is compatible with lock-in detection, allowing low-bandwidth measurements. This results in a substantial improvement of the imaging dynamic range, making it comparable to OCT, while maintaining the simplicity of SI.

Consider two plane electromagnetic waves interfering at the output of the interferometer. The resulting spectrum is:

$$S(\omega)=|E_1(\omega)|^2+|E_2(\omega)|^2+2E_1(\omega)E_2(\omega)\cos(\phi_1(\omega)-\phi_2(\omega)-\omega\tau) \quad (1)$$

where $\omega$ is the frequency, $S(\omega)$ is the spectrum at the output of the interferometer, $E_1(\omega)$ and $E_2(\omega)$ are the magnitudes of the electric fields in each arm of the interferometer, $\phi_1(\omega)$ and $\phi_2(\omega)$ are the phases of the two waves, and $\tau$ is the optical delay between the two arms of the interferometer. The first two terms are the DC spectral terms from the light source. The third term contains the desired information.

If one adds a small time delay, $\Delta\tau$, and subtract that spectrum from the spectrum in Eq. (1), we get the following difference spectrum $S_{dif}(\omega)$:

$$S_{dif}(\omega)=E_1(\omega)E_2(\omega)[\cos(\phi_1(\omega)-\phi_2(\omega)-\omega\tau)-\cos(\phi_1(\omega)-\phi_2(\omega)-\omega(\tau+\Delta\tau))] \quad (2)$$

By applying familiar trigonometric identities, Eq. (2) can be simplified to the following form:

$$S_{dif}(\omega)=E_1(\omega)E_2(\omega)[\cos(\phi_1(\omega)-\phi_2(\omega)-\omega\tau)-\cos(\phi_1(\omega)-\phi_2(\omega)-\omega\tau)\cos(\omega\Delta\tau)-\sin(\phi_1(\omega)-\phi_2(\omega)-\omega\tau)\sin(\omega\Delta\tau)] \quad (3)$$

If $\Delta\tau$ is set such that $\omega\Delta\tau\approx\pi$ ($\Delta\tau$ is reasonably assumed to be much smaller than the inverse of the light source bandwidth), then Eq. (3) reduces to:

$$S_{dif}(\omega)\approx 2E_1(\omega)E_2(\omega)\cos(\phi_1(\omega)-\phi_2(\omega)-\omega\tau) \quad (4)$$

Following from the above description, when a $\pi$ phase shift modulation is introduced into the reference arm, the DC and autocorrelation terms are cancelled and there is two-fold increase of the useful signal amplitude.

A schematic diagram of an apparatus 10 according to the invention used to obtain images of test targets 22, such as biological samples, is shown in FIG. 1. The DSI instrument is based on a Michelson-type interferometer. A laser 12 producing a broadband output, preferably either a mode-locked Ti:sapphire laser ($\lambda$=800 nm, FWHM=27.3 nm) or a superluminescent diode ($\lambda$=840 nm, FWHM=12.3 nm) is used as the light source, which light passes through mode matching optics 24 to beamsplitter 26. The interferogram is spectrally resolved 14, such as with a ¼ meter imaging spectrograph, and detected via detector 16, preferably with an array detector such as a 16-bit CCD camera. The mirror 18 in the reference arm of the interferometer is dithered, preferably with a piezo-translator at f=70 Hz, to introduce a $\pi$ phase shift to the reference beam. To get a single depth profile, the spectra at the two extreme positions of the dithered mirror are acquired, and a Fourier transform is performed on the difference spectrum via computer 20. While this detection system does not completely eliminate the dynamic range problem inherent in CCD's, it demonstrates the basic utility of DSI. To fully test DSI, lock-in detection experiments were also performed (see below).

Figure 2:
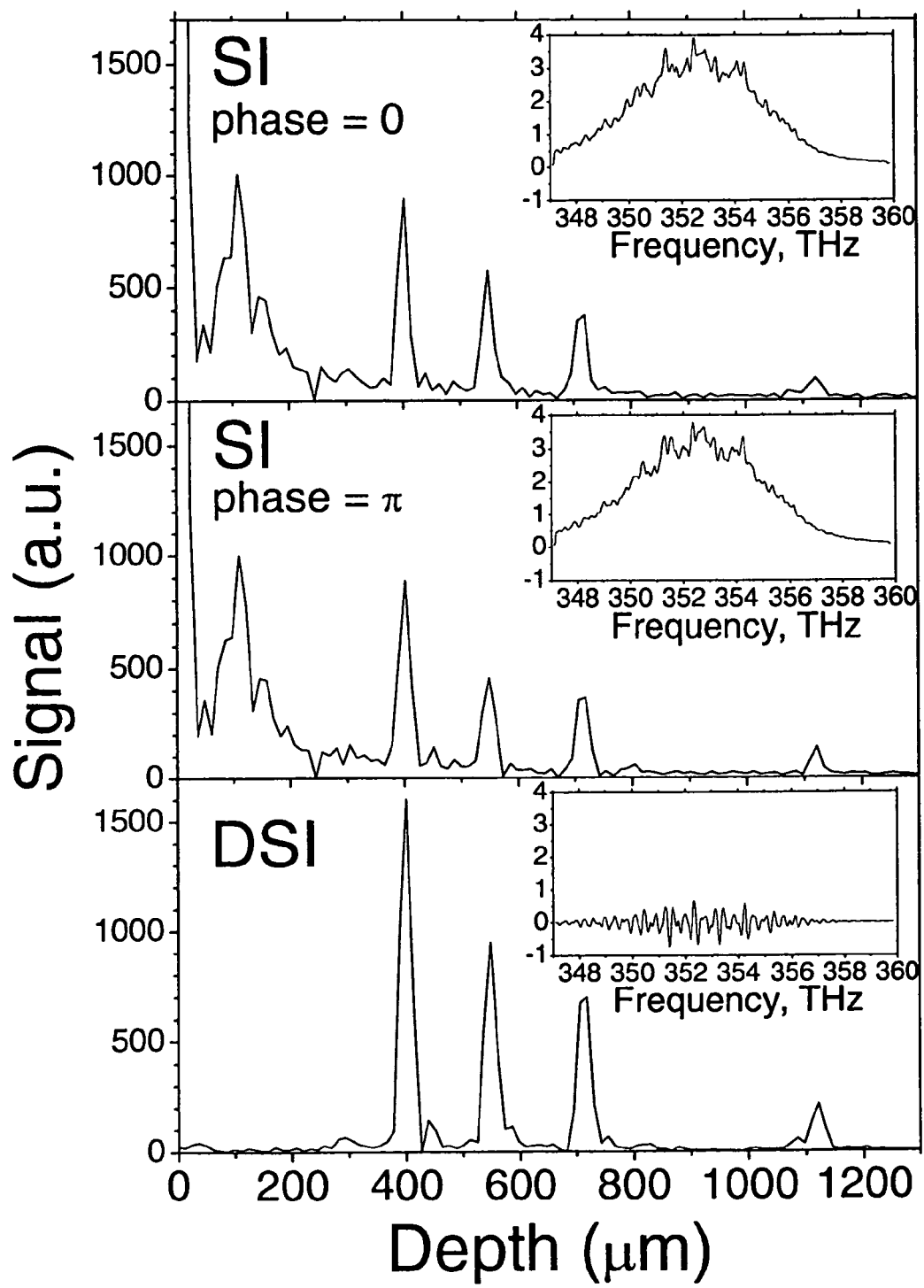
FIG. 2 is the interferograms (insets) and their Fourier transforms that produce one-dimensional depth profiles of a test sample constructed of microscope glass cover slides: (a) SI image with zero displacement of the reference arm mirror; (b) SI image with a $\pi$ phase shift in the reference arm; (c) DSI image. The light source is a superluminescent diode centered at ~840 nm with a bandwidth of 12.3 nm.

FIG. 2 compares the one-dimensional SI scans (obtained with the phase shifts of 0 and $\pi$) to the DSI scan acquired for a test sample constructed of microscope glass cover slides. It is seen from FIG. 2 that DSI with differential detection provides a very efficient suppression of the background features, including the DC and autocorrelation terms in the vicinity of the position of the reference plane (zero depth). As expected, the intensities of the DSI signal peaks increase about twice their original value in the SI scans.

Figure 3:
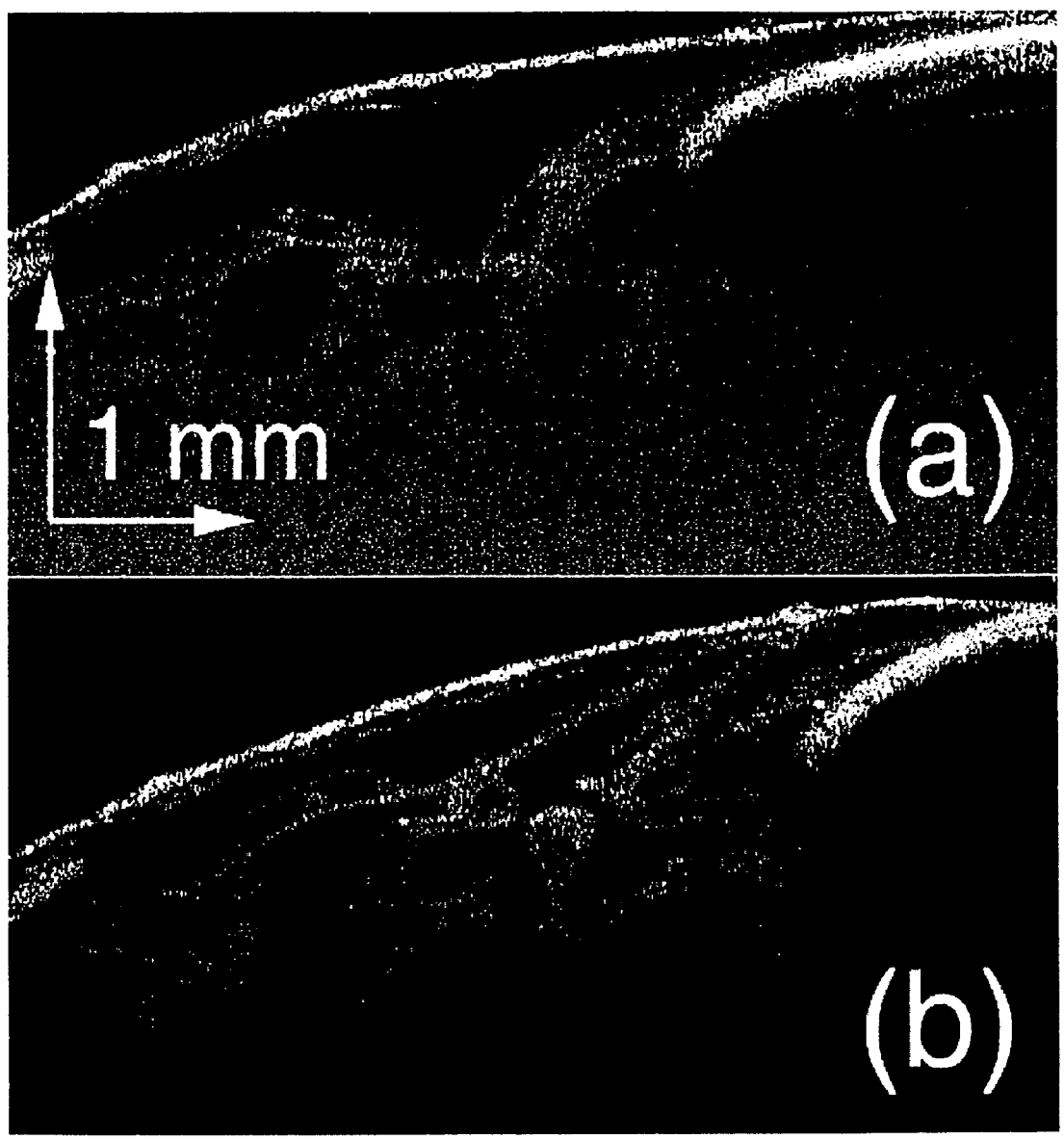
FIG. 3 are the cross-sectional (depth vs. lateral position) images (500×256 pixels) of a region of a *Xenopus* tadpole head obtained by DSI without averaging (a) and with averaging of 100 Fourier-transformed DSI spectra for each lateral position (b). The light source is the superluminescent diode.

The axial resolution is 11 µm with the laser and 24 µm with the SLD light source; the lateral resolution is 10 µm. As in SI, the axial resolution is limited by the bandwidth of the light source, while the lateral resolution is determined by the focusing conditions (f=2.52 cm, in these experiments). The free-space depth range is limited by the spectral resolution of the spectrograph, and is about 0.3 cm for the present instrument. The dynamic range, measured by inserting different neutral density filters in the sample arm of the interferometer, was found to be about 75 dB. Unlike SI, DSI removes the background features allowing the image signal-to-noise ratio, which is determined by the random noise of the baseline, to be improved by averaging multiple images. By averaging 100 differential spectra, a dynamic range of 94 dB was obtained. Further gains in dynamic range result from optimization of the detection system. FIG. 3 illustrates the improvement in the quality of a DSI image (500×256 pixels) of a region of the head of a *Xenopus Laevis* (African clawed frog) tadpole by averaging over 100 Fourier-transformed differential spectra for each scan. With the averaging, the effective imaging rate was 5.6 ms/pixel.

To demonstrate the advantages of using lock-in detection, experiments were performed with a scanning monochromator and single-channel lock-in detection with a dithering frequency of 1.4 kHz. A significant enhancement in the dynamic range up to 105 dB was observed. With the use of a photodiode array detector with true lock-in detection for each individual photodiode, improvement of the image acquisition rate to ≈10 Hz for video-rate imaging is possible. For example, to achieve a 10 Hz rate for a 2D-image consisting of 100 1D-depth profiles, the acquisition rate should be one 1D-scan per 1 ms. There are no fundamental limitations in achieving that rate. At present, with one-channel lock-in detection we obtain high-quality differential spectra with a dithering frequency of up to approximately 5 kHz and time constant of the lock-in amplifier of approximately 300 µs. Note, for an imaging rate of one 1D-scan per 1 ms, the noise equivalent bandwidth will be ≈1 MHz for OCT and ≈1 kHz for DSI. This means that, theoretically, with the same power of the light source, quantum efficiency and dynamic range of the detectors, multi-channel DSI can provide a signal-to-noise ratio (SNR) of about a factor of 30 higher than OCT, assuming the noise scalar as the square root of the bandwidth.

The invention provides a simple and powerful new modification to SI that provides effective background suppression and greatly improves the obtainable dynamic range. For biomedical applications, the multi-channel version of DSI is competitive with OCT in image quality and acquisition rate, while being more robust and mechanically simpler.

Differential spectral interferometry preserves the features of OCT and SI alone while providing the following advantages:

DSI is optically and mechanically simple and reliable. DSI is based on a fixed interferometer—the reference arm requires only a small dither of a few microns rather than several millimeters greatly simplifying alignment and design.

DSI is inherently parallel leading to faster imaging rates. DSI uses frequency domain interferometry allowing the entire interferogram to be recorded simultaneously.

DSI reduces system bandwidth requirements resulting in clearer images. The inherent parallel data acquisition of DSI reduces the bandwidth of the detection electronics from a few MHz to a few 10's of Hz.

DSI hardware is similar to OCT, speeding regulatory approval.

In determining the utility of the invention, the following questions present themselves:

(1) Can DSI provide sufficient spatial resolution and signal-to-noise ratios for imaging tissue microstructures? Specifically, are axial resolutions near 10 µm achievable by this method?

(2) Can DSI provide sufficient contrast for cross-sectional tissue imaging? Specifically, can a high resolution CCD camera (or other array detector) provide the necessary dynamic range for imaging to depths of a few mm in scattering media?

(3) How does imaging DSI compare with current coherence imaging methods? Will video rate imaging ultimately be achievable in a commercial instrument?

In testing, questions (1) and (2) were answered affirmatively, i.e., it was demonstrated that differential spectral interferometry can be used to image biological tissues. In addressing question (3), DSI can be used for high-speed acquisition of cross-sectional images of biological objects with the required resolution and dynamic range. The image quality is comparable to that of OCT, and there are no fundamental limitations which will prevent acquiring images at video rates.

Optical Coherence Tomography

Optical coherence tomography (OCT) is the application of optical coherence reflectometry (OCR) to cross-sectional imaging in biological tissues. Optical coherence reflectometry is a technique that has been used for many years for high resolution phase and distance measurements, and surface contour mapping in such materials as optical components, eye structures, and integrated circuits. Since 1991, development and demonstration of OCT for a variety biomedical applications has been pursued.

Optical coherence reflectometry (or tomography) is essentially a time domain technique where distance is measured using optical delay times. A spectrally broad, low coherence light beam, such as output from a femtosecond laser or super luminescent diode (SLD), is split into sample and reference beams within a Michelson interferometer. The sample beam is directed into the specimen, while the reference beam travels a path of nearly equal distance. The reference arm length is rapidly modulated. Light returning from the sample recombines with the reference beam at the beam splitter. A single element, AC detector is used to detect interferometer output. Since the light has a short coherence length, interference occurs only when the optical time-of-travel through each arm of the interferometer is the same. The interferometer pattern yields the spatial profile of the sample directly.

Optical coherence interferometry techniques, such as OCR and OCT, actually measure differences in phase between the reference and sample arms. Different optical path lengths between the two arms, whether resulting from an actual difference in distance traveled, or a difference in index of refraction, result in a phase shift between the two beams. This phase shift is recorded in an interference pattern. Knowing the length of the reference arm and the index of refraction of the sample allows determination of the depth from which light is reflected or backscattered in the sample. Rapidly scanning the reference arm length allows signal from varying depths in the sample to be collected, while scanning the beam across the specimen provides imaging in the transverse plane. Multiple axial scans are made at a series of lateral positions to provide a 2-dimensional cross-sectional map of reflection or back-scattering locations in the sample.

Most high resolution optical imaging techniques, such as confocal, two-photon and near-field methods, require high intensity laser sources. In confocal and multi-photon microscopes, the longitudinal (depth) resolution is determined by the beam focus and collection apertures. For OCT the longitudinal resolution is inherent in the light source—it is determined by the coherence length. This means that a super luminescent diode (SLD) can be used while still maintaining good resolution; 15 µm depth resolution has been demonstrated with an SLD source. As with other optical imaging methods, transverse resolution is determined by beam focusing and apertures.

OCT is often implemented with optical fibers for both interferometer arms. This makes the technique suitable for in vivo and endoscope applications. Other advantages are that low powers (micro- to milliwatts) and near infrared wavelengths, where tissues and cells are most transparent, are used. This avoids photo-induced damage to the specimen. In the past few years, research into OCT applications including endoscopic OCT instruments, Doppler OCT for blood flow imaging, in vivo measurements in several different organs, and work towards disease and cancer detection have been reported. Other developing applications include assessment of tissue during microsurgery, and imaging of embryonic and neural tissue.

One drawback to OCT is that real-time imaging is not simple to achieve. The need for a high-bandwidth (up to a few MHz) detector precludes the use of cameras at high frame rates. Fast imaging also requires high speed modulation of the reference arm, which is not feasible using inexpensive mechanical components. New advances such as a Fourier domain optical delay line have made video rate OCT possible, but high bandwidth electronics are still required even when parallel detection is used. DSI is a frequency domain technique, making it inherently parallel. As a result, the bandwidth of the electronics is greatly reduced, lowering noise.

Spectral Interferometry

Spectral interferometry (SI) has been applied to high resolution distance and phase measurements in a variety of applications. However, until recently SI has received little attention in the biomedical optics field. One notable exception is a 1998 publication by Häusler and Lindner on dermatological applications of SI, which they term "Spectral Radar." G. Hausler, et al., "Coherence radar and spectral radar—new tools for dermatological diagnosis", *J. Biomed. Opt.* 3, 21–31 (1998). Other biomedical applications have been in ophthalmology. A. F. Fercher, et al., "Measurement of intraocular distances by backscattering spectral interferometry", *Opt. Commun.* 117, 43–48 (1995).

Like OCT, SI is an optical technique that uses an interferometer and a low coherence, spectrally broad light source. However, with SI, the interferometer is fixed; instead of scanning the reference arm, the interferometer output is spectrally dispersed before detection. The signal from the sample consists of a superposition of monochromatic waves returning from different depths in the sample. These interfere with corresponding components from the fixed reference arm creating a spectral interferogram. The interferometer output is sent through a spectrograph to resolve the interference fringes.

Depth information is encoded in the frequency of the fringes and can be extracted using simple Fourier transform that can be performed in only a few microseconds. With SI, all depth information is acquired simultaneously in an inherently parallel manner using a CCD array, eliminating the need for axial reference arm scans. The spectrum of the interferometer output (sum spectrum), $I_{SI}(\omega)$, is given by $$I_{SI}(\omega) = I_R(\omega) + I_S(\omega) + 2\sqrt{I_R(\omega) I_S(\omega)} \times \cos(\phi_S(\omega) - \phi_R(\omega) - \omega\tau) \quad (5)$$

where $I_{SI}(\omega)$ is the interferometer output spectrum, expressed as intensity as a function of optical frequency w. $I_R(\omega)$ is the spectrum of the light returning from the reference arm while $I_S(\omega)$ is the spectrum of the light returning from the sample arm. $\phi_R(\omega)$ is the reference arm phase, $\phi_S(\omega)$ is the sample arm phase, and t is a fixed optical delay between the two arms.

The first two terms in Eq. 5 are simply the reference and sample arm spectra. The third term—the interference between the reference and sample arms—contains the depth (phase) information. As with OCT, a phase delay can result from both differences in distance between the reference arm and backscattering loci in the sample and from differences in index of refraction. It is necessary to know the sample index of refraction in order to quantitatively determine depth.

To facilitate extracting the depth information from the SI output, the delay, $\tau$, is chosen to yield fringes in the sum spectrum, i.e., so that the optical paths are nearly, but not exactly, equal. This delay then remains fixed, and optical path differences resulting from back-scattering from various depths in the sample are encoded in the interference fringes. The spectral fringes have a period inversely proportional to the optical path difference between the two beams.

The first step is to subtract the individual spectra, $I_R(\omega)$ and $I_S(\omega)$, from the total signal in order to isolate the spectral interferogram, $S(\omega)$, where $$S(\omega)=2\sqrt{I_R(\omega)I_S(\omega)}\times cos(\phi_S(\omega)-\phi_R(\omega)-\omega\tau) \quad (6)$$

By Fourier transforming the result, $S(\omega)$, one obtains $$\mathfrak{J}^{-1}[S(\omega)]=f(t-\tau)+f(-t-\tau) \quad (7)$$

where f(t) is the correlation product between the reference and sample fields. In this example, reflection from a single depth in the sample results in a simple function of intensity versus time delay. Note that "mirror images" of f(t) occur at positive and negative delays. If the time delay results purely from reflection or scattering, then time corresponds directly to distance. In tissue samples, the index of refraction must also be taken into account.

$I_S(\omega) \approx I_R(\omega)$ when there is no significant absorption that changes the spectral profile of the light returning from the sample (except for possible attenuation at all frequencies due to multiply scattering media). In this case, subtraction of $I_S(\omega)$ and $I_R(\omega)$ before the Fourier transform is feasible. However this is not necessary. If the individual spectra are left in the interferogram, they will appear as a background feature centered around zero in the time domain and generally can be removed by appropriate filtering. However, the dynamic range issue still remains a problem.

Complex, multi-component signals are also observed for biological tissues. In highly scattering samples, it may be necessary to use a weighting function (typically exponential) to account for attenuation due to multiple scattering of light returning from greater depths. Otherwise, the mathematical treatment remains relatively simple, requiring only Fourier transformation of the spectral interferogram.

Differential Spectral Interferometry

DSI is a modification and improvement of SI that requires only a small dithering of the reference path of the interferometer. A differential spectral interferogram is obtained by subtracting the individual spectra acquired at two slightly different positions of the dithered mirror. Instead of a fixed mirror in one arm of the interferometer, a mirror is used that can be dithered slightly (a few microns at most). To complete the subtraction at the dither frequency, synchronous detection (preferably lock-in detection) is used, eliminating the spectral contributions from the individual pulses that improves the dynamic range. A Fourier transform is performed on the differential spectrum to obtain the sample depth profile. By optimizing the dither to a $\pi$ phase shift, the spectral profile of interest coherently adds while the deleterious background is efficiently removed.

Consider two plane electromagnetic waves interfering at the output of the interferometer. The spectrum of the two electric fields is given by:

$$S(\omega)=|E_1(\omega)e^{i\phi_1(\omega)-i\omega t_1}+c.c.+E_2(\omega)e^{i\phi_2(\omega)-i\omega t_2}+c.c.|^2 \quad (8)$$

where $S(\omega)$ is the spectrum, $E(\omega)$ is the magnitude of the electric field (and hence real), $\phi(\omega)$ is the phase as a function of $\omega$, and t is the time and c.c. is the complex conjugate. Completing the square yields:

$$S(\omega)=|E_1(\omega)|^2+|E_2(\omega)|^2+E_1(\omega)E_2(\omega)(e^{i\phi_1(\omega)-i\phi_2(\omega)-i\omega(t_1-t_2)}+e^{i\phi_2(\omega)-i\phi_1(\omega)-i\omega(t_2-t_1)}) \quad (9)$$

which gives:

$$S(\omega)=|E_1(\omega)|^2+|E_2(\omega)|^2+E_1(\omega)E_2(\omega)\cos(\phi_1(\omega)-\phi_2(\omega)-\omega\tau) \quad (10)$$

where $\tau$ is the difference between $t_1$ and $t_2$.

If one adds a small time delay, $\Delta\tau$, to the time delay between the electric fields, $\tau$, and subtracts that spectrum from the spectrum in Eq. 10, one gets:

$$E_1(\omega)E_2(\omega)[\cos(\phi_1(\omega)-\phi_2(\omega)-\omega\tau)-\cos(\phi_1(\omega)-\phi_2(\omega)-\omega(\tau+\Delta\tau))] \quad (11)$$

Using:

$$\cos(\theta_1-\theta_2)=\cos\theta_1\cos\theta_2-\sin\theta_1\sin\theta_2 \quad (12)$$

one gets:

$$E_1(\omega)E_2(\omega) \quad (13)$$
$$\begin{bmatrix} \cos(\phi_1(\omega)-\phi_2(\omega)-\omega\tau)-\cos(\phi_1(\omega)-\phi_2(\omega)-\omega\tau)\cos(\omega\Delta\tau) \\ -\sin(\phi_1(\omega)-\phi_2(\omega)-\omega\tau)\sin(\omega\Delta\tau) \end{bmatrix}$$

If $\Delta\tau$ is set such that $\omega\Delta\tau \sim \pi$, then the above equation reduces to:

$$2E_1(\omega)E_2(\omega)\cos(\phi_1(\omega)-\phi_2(\omega)-\omega\tau) \quad (14)$$

Thus, the signal of interest, $E_1(\omega)E_2(\omega)$, coherently adds while the background terms are subtracted. The experimental work demonstrates this.

Even when $\omega\Delta\tau$ is close to $\pi$, equation 13 can be approximated as:

$$E_1(\omega)E_2(\omega)[2\cos(\phi_1(\omega)-\phi_2(\omega)-\omega\tau)-\sin(\phi_1(\omega)-\phi_2(\omega)-\omega\tau)\sin(\omega\Delta\tau)] \quad (15)$$

The second term in equation 8 acts a modulation on the first term producing side bands on $\tau$ spaced by $\Delta\tau$. As long as the resolution $>>\lambda/2$, the spacing of the side bands cannot be resolved and does not affect the resolution. For very wide bandwidth sources $\sim\omega_0/10$ or more (where $\omega_0$ is the center frequency), equation 13 cannot be approximated.

When a $\pi$ phase shift modulation is introduced into the reference arm, the DC and autocorrelation terms (included in the $|E_1(\omega)|^2$ and $|E_2(\omega)|^2$ terms in Eq. 10) are cancelled, and there is two-fold increase of the useful signal amplitude. The differential spectrum can be obtained in the AC mode, which greatly reduces the noise equivalent bandwidth. With the use of a photodiode array detector with lock-in detection for each individual photodiode, the differential spectra can be collected in an inherently parallel way. Both the reduced noise equivalent bandwidth and the multichannel character of data acquisition lead to an increase of the signal-to-noise ratio. Our estimates show that multichannel DSI may provide a signal-to-noise ratio of a factor of 30 higher than OCT. In addition, if the full dynamic range of the detectors can be used, an additional improvement in the signal-to-noise ratio of $N^{1/2}$, where N is the number of detectors, may be obtained.

Taking the difference signal between a small dither in the relative phase between the arms of the interferometer is not the only way to reject the DC background, autocorrelation terms and 1/f noise. According to J. Schmit, et al., "Extended averaging technique for derivation of error-compensating algorithms in phase shifting interferometry," Appl. Opt. 34, 3610 (1995), arithmetically combining several different interferograms with several different phase differences can be used to determine either the real (cosine) part of the imaginary (sine) part of the interferogram, which will reject DC background and autocorrelation terms. However, it is also important to measure the component interferograms (that are arithmetically combined to obtain the real and the imaginary parts of the interferogram of interest) in a manner that rejects 1/f noise. Thus, the component interferograms must be obtained as close to simultaneously as possible.

For example, suppose the interferogram of interest is the arithmetic combination of six different interferograms, each labeled $I_1$ through $I_6$ and each with its own relative phase, and the interferogram of interest is given by $-I_1+5I_2+2I_3-10I_4+3I_5+I_6$. The low frequency cutoff is determined by the amount of time required to measure the set of six interferograms. If averaging is required, complete sets of the interferograms should be averaged, which increases the low frequency cutoff (the order in which the component interferograms is taken is not important) so that it has a high enough frequency to reject 1/f noise. Averaging each component interferogram separately lowers the frequency of the low frequency cutoff (makes the low frequency cutoff closer to DC) and, therefore, does not reject the 1/f noise.

Consequently, taking the data in the order $I_1$, $I_2$, $I_3$, $I_4$, $I_5$, $I_6$, $I_1$, $I_2$, $I_3$, $I_4$, $I_5$, $I_6$, $I_1$, $I_2$, $I_3$, $I_4$, $I_5$, $I_6$ is not the same as taking the data in the order $I_1$, $I_1$, $I_1$, $I_2$, $I_2$, $I_2$, $I_3$, $I_3$, $I_3$, $I_4$, $I_4$, $I_4$, $I_5$, $I_5$, $I_5$, $I_6$, $I_6$, $I_6$. In the first case, the low frequency cutoff is approximately given by the reciprocal of the time required to measure the first six interferograms, which we will call t. The low frequency cutoff is then approximately 1/t. In the second case, the low frequency cutoff is approximately the reciprocal of the time required to measure all 18 interferograms, which is 3 t. Thus, the low frequency cutoff is a factor of 3 smaller in the second case. If the first case is used to average the interferogram, all the frequencies between 1/t and DC are rejected. However, in the second case, only the frequencies between 1/(3 t) and DC are rejected—all the noise in the frequencies between 1/(3 t) and 1/t is integrated into the measurement with no gain in signal.

Note that the present invention can also be used with the variation of spectral interferometry in which the broadband light source is replaced with a swept wavelength source. Because the wavelength is swept, the need for a spectrometer is removed and a single detector can be used instead of an array detector, which simplifies the device. The disadvantage is that the data collection time is increased because the data for each wavelength cannot be taken in parallel.

Imaging Spectral Interferometer

A spectral interferometer was constructed using a Melles Griot 03 BSC 029 cube beamsplitter (BS), two Newport 10D520ER.2 silver-coated pyrex flat mirrors, and two Newport GPX043LR.16 GRADIUM singlet lenses (f=2.52 cm). The spectra were analyzed using a ¼ meter Chromex imaging spectrograph combined with a cooled 16-bit CCD camera (C7041, Hamamatsu). Spectral interferometry was performed using a broad band, low coherence length, passively mode-locked Ti:sapphire laser (KM Labs) or a super luminescent diode (LDN-16, Volga Technology). The emission spectra of the laser and the super luminescent diode (SLD) have bandwidth FWHM of $1.3 \times 10^{13}$ Hz (27.3 nm) and $0.6 \times 10^{13}$ Hz (12.3 nm), respectively. The instrument was constructed to use both types of light source. The schematic diagram of the instrument is shown in FIG. 1.

The mirror in the reference arm of the interferometer ("Dithered mirror" in FIG. 1) is preferably mounted on a ThorLabs KC1-PZ piezo translator, which allows high-precision translation of the mirror within up to 5 µm along the optical axis using a ThorLabs MDT693 piezo controller.

The sample holder ("Test target" in FIG. 1) is mounted on a 9065-XYZ New Focus XYZ (3 axis) translation stage. The position of the sample in the XY-plane (perpendicular to the laser beam) is controlled by two Newport CMA-12CCCL motors. The CCD-camera, motorized XYZ translation stage, and the controller of the piezo translator are interfaced to a computer using software created in National Instruments LabView® graphical development environment.

To evaluate the spatial resolution of the instrument and to obtain images of test samples and biological tissues, we used high-speed differential detection. The CCD camera is capable of acquiring spectra at a speed of up to 160 Hz in binned mode. In these experiments, the CCD camera readout rate was set at 140 Hz. Thus, the delay line was dithered at 70 Hz, synchronized to the readout of the CCD camera. To get a single depth profile, the spectra at the two extreme positions of the mirror were acquired, and the Fourier transform was performed on the difference spectrum. While this detection system does not completely eliminate the dynamic range problem inherent in CCDs, it demonstrates the utility of DSI. A true lock-in detection scheme is discussed below.

Figure 4:
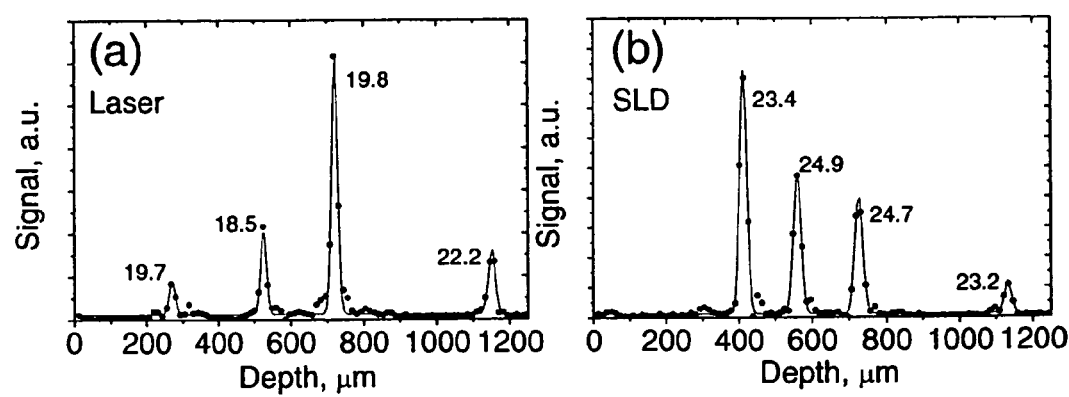
FIG. 4 is the DSI spectra of test samples constructed of glass slides obtained with the Ti:sapphire (a) and superluminescent diode (b) light sources. The FWHM of the peaks are indicated near the peaks.

FIG. 4 shows an example of experimental SI and DSI spectra and the resulting depth profiles of a sample constructed of microscope cover slides. The two SI spectra correspond to a π phase shift introduced to the reference beam. Both SI profiles look similar, showing the peaks at 400 µm, 550 µm, 715 µm, and 1120 µm that correspond to reflective surfaces of the sample. Besides the useful signal peaks, the SI profiles contain strong background, which gains overwhelming amplitude at depth close to zero (DC term). As seen from FIG. 4, DSI provides a very efficient suppression of the background (including the DC term). Moreover, the intensities of the DSI signal peaks increase about twice their original value in the SI scans. These features of DSI, which could be anticipated from the theoretical description of the method (see previous section on DSI), provide dramatic improvement of the SI technique in terms of the signal-to-noise ratio and image quality.

Spatial Resolution

The axial and lateral resolution of DSI images are basically the same as those of SI. Namely, the axial resolution is determined by the wavelength and bandwidth of the light source, and the lateral resolution is determined by the incident light focusing conditions.

FIG. 4 shows representative examples of depth profiles of test samples constructed of glass slides, obtained with the laser (4a) and SLD light source (4b). The peaks were fitted by the Gaussian function. The FWHM of the fitted peaks are indicated in the figures. The FWHM of the peaks were found to be 20±2 µm and 24±2 µm for the laser and SLD light sources, respectively. Theoretical bandwidth-limited peak widths are ≈10 µm for the laser (bandwidth $1.3 \times 10^{13}$ Hz) and ≈22 µm for the SLD ($0.6 \times 10^{13}$ Hz). For the SLD light source, the experimental peak width is close to the bandwidth-limited value. Theoretical resolution of the laser light source and the obtained resolution are different because the spectral window of the spectrometer does not allow detection of the whole emission bandwidth of the laser. The spectral window is determined by the spectrograph/CCD camera spectrum analyzer, whose performance is optimized to achieve the best spectral resolution. High spectral resolution provides good imaging depth (almost 3 mm in free space, with this instrument) at the expense of spatial resolution. The use of a different (lower resolution) spectrograph would improve the axial spatial resolution, however the imaging depth would be worse. As seen below, with true lock-in detection, the bandwidth-limited axial resolution is achievable with the Ti:sapphire laser light source.

Figure 5:
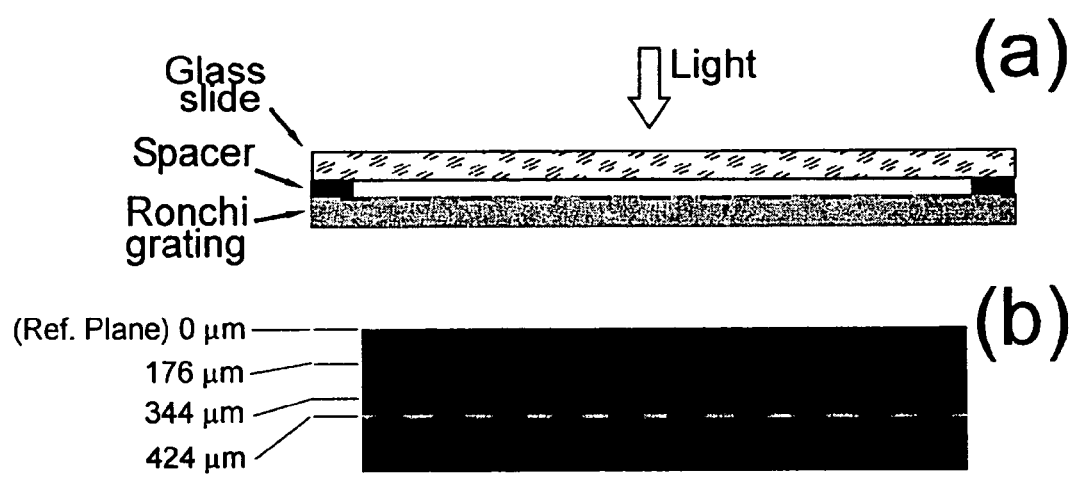
FIG. 5 is the schematic diagram of a test sample constructed of a Ronchi grating and a microscope cover slide (a) and the corresponding cross-sectional DSI image (b). The light source is a Ti:sapphire laser.

FIG. 5 shows an example of a cross-sectional scan of a test sample constructed of a Ronchi grating (40 lines/mm) and a microscope cover glass slide (thickness 110 μm). The glass slide was attached to the grating through spacers (thickness 80 μm). The sample is shown schematically in FIG. 5(a). The DSI 2D-scan produces a clear image of the surface of the Ronchi grating (at 424 μm) and two surfaces corresponding to the glass slide (at 176 μm and 344 μm). The spacing between the glass slide and the grating, as well the thickness of the glass slide, evaluated from the DSI image, agree well with the corresponding thicknesses, measured independently with a digital caliper (note, the thickness of the glass slide obtained from the image, 168 μm, is the actual thickness multiplied by the index of refraction of the glass, n≈1.5).

Evaluation of the Dynamic Range.

To evaluate signal-to-noise (S/N) ratio of the invention, a method similar to that described by Hausler and Lindner was employed. One determines the minimum intensity of light reflected from the sample (relative to the intensity of the incident light) that can be observed with the S/N ratio equal to unity. In other words, the dynamic range of the setup is evaluated.

Figure 6:
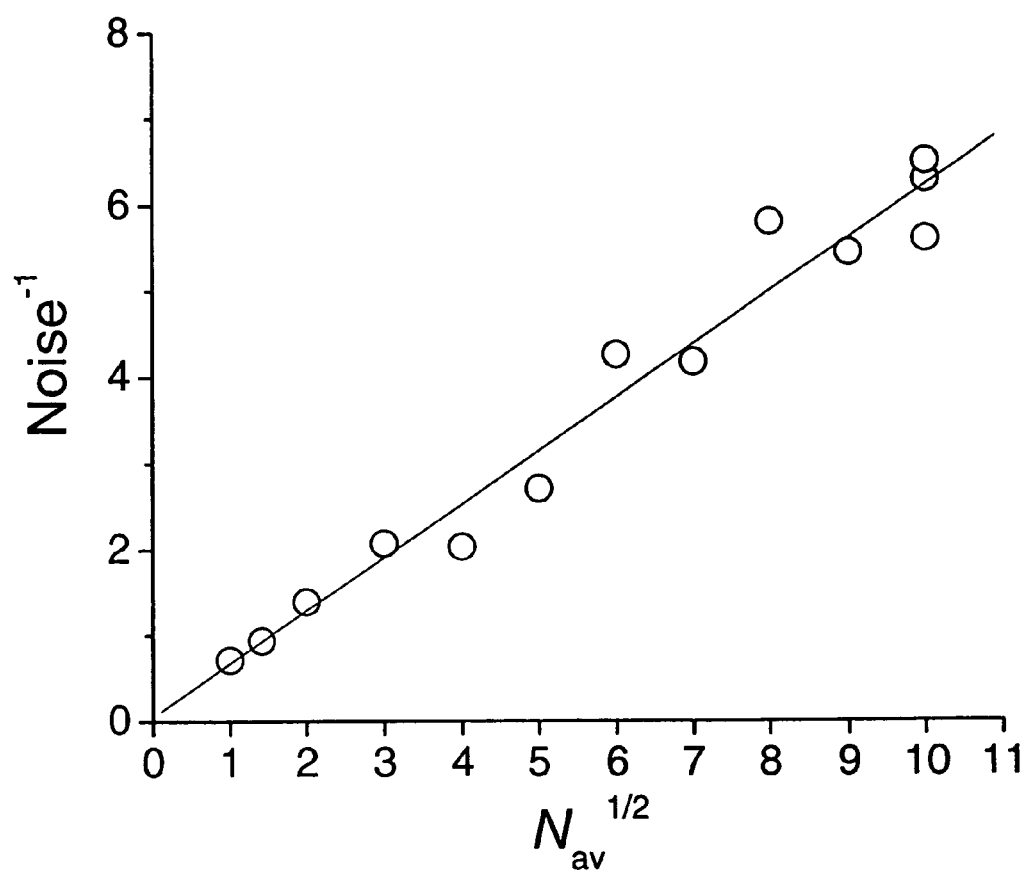
FIG. 6 is a plot showing the reciprocal of the noise amplitude versus square root of the averaging number (points) and a linear fit to the experimental data (line).

First, consider the noise. As mentioned above, DSI efficiently suppresses the background that is inherent to SI imaging. With SI, the imaging dynamic range is limited by the background rather than by noise, which prevents improvement of the image quality by averaging multiple scans. To check if the random noise limit can be achieved in DSI, the noise of the baseline of DSI images of a mirror was measured with averaging over 1 to 100 scans. The results are shown in FIG. 6. It is seen from FIG. 6 that the reciprocal of the noise scales linearly with the square root of the number of averaged scans. This indicates that the DSI dynamic range is limited by random noise, and that the quality of the image can be efficiently enhanced by averaging.

Figure 7:
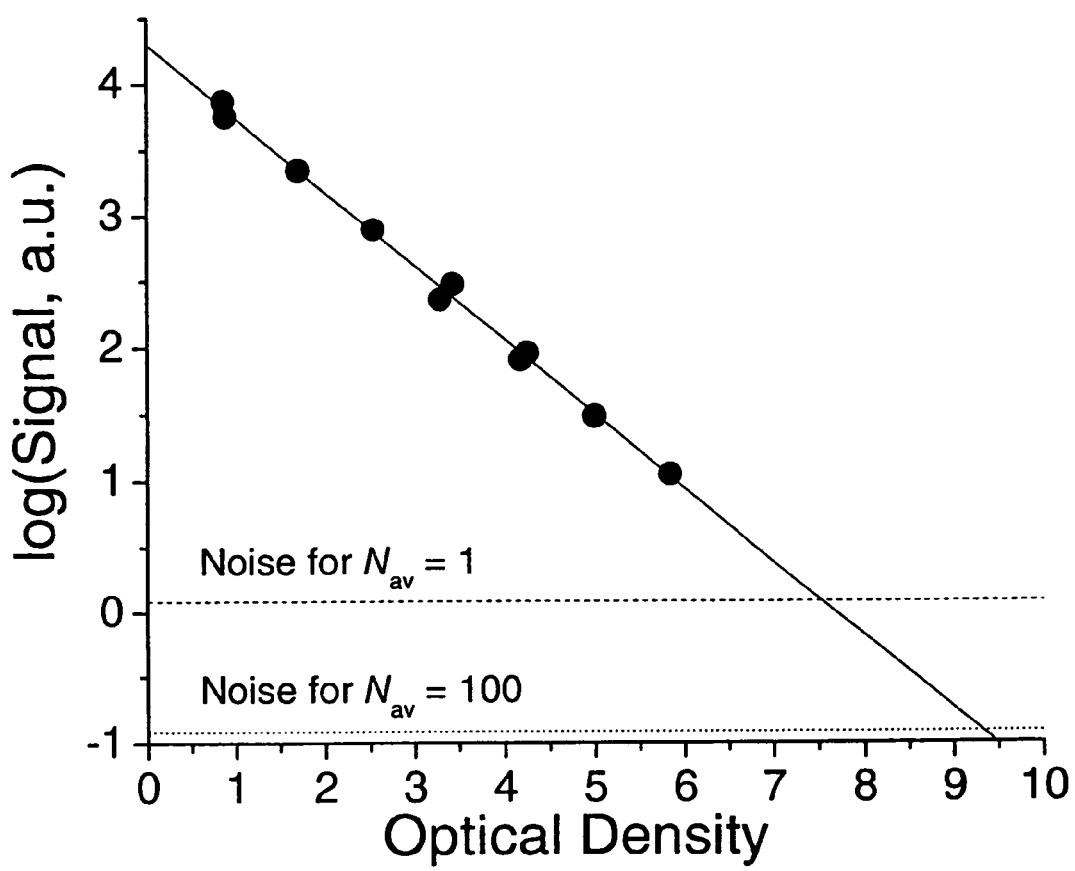
FIG. 7 is a plot evaluating the dynamic range of the DSI imaging instrument. Dashed lines indicate the noise levels for averaging of the signal over 1 and 100 scans. The light source is a Ti:sapphire laser.

To measure the dynamic range, an aluminum-coated mirror was used as a sample. The intensity of the peak corresponding to the image of the mirror was measured with different neutral density (ND) filters inserted in the sample arm of the interferometer. FIG. 7 shows the peak intensity plotted versus the ND filter optical density (OD). Because the light in the sample arm of the interferometer passes through the filter twice, the OD was calculated as twice the optical density of each ND filter. For each filter, OD was determined experimentally by measuring the Ti:sapphire laser light attenuation. The dashed lines in FIG. 7 indicate the noise level with the signal averaged over 1 and 100 scans. The experimental points in FIG. 7 can be fitted by a straight line, which intersects the shot noise level at OD=7.4, thus yielding an estimate of the dynamic range of the detection system, equal to 74 dB. This result means that one can detect the intensity of light reflected from the sample that is as low as $4 \times 10^{-8}$ of the incident light intensity. This is comparable to the dynamic range data for analogous spectral interferometry imaging setups.[15,16] Unlike SI, the imaging quality of DSI can be improved by averaging. As seen in FIG. 7, by averaging over 100 scans, the dynamic range is increased to about 94 dB.

Contrast and Resolution of Images in Scattering Media

The effect of light-scattering media on the contrast and axial resolution of DSI images of tissue phantom samples was investigated. In these experiments, both the Ti:sapphire laser and SLD were used as the light sources. The pseudo-lock-in detection scheme described above was used. Two tissue phantom samples were constructed by attaching thin glass slides (thickness 110 μm) to the back surface of the glass plate through spacers of different thickness, 160 μm and 360 μm for the two samples, respectively. DSI images of these samples, immersed in light-scattering fluid, were taken. Diluted Intralipid (Phospholipid stabilized soybean oil 20% fat emulsion) purchased from SIGMA was used as scattering medium. As expected, the light-scattering medium significantly decreases the contrast of the images. From this experiment, the following effective scattering coefficient: $\mu_s=34$ percent$^{-1}$ cm$^{-1}$ was obtained. The obtained $\mu_s$ is in good agreement with the literature data. See, e.g., H. G. Van Staveren, et al., "Light scattering in intralipid-10% in the wavelength range of 400–1100 nm," *Appl. Opt.* 30,4507–4514 (1991). Peak widths were also measured as a function of Cd. No effect of the light scattering was observed.

In combination with the dynamic range measured for our instrument, these data provide an estimate of the maximum imaging depth that can be achieved in imaging real human tissues. A 10% Intralipid emulsion is frequently used for modeling the scattering properties of typical human tissues. The effective scattering coefficient of 10% Intralipid is ≈340 cm$^{-1}$. Combined with the measured 74 dB dynamic range, this yields a maximum imaging depth of about 500 μm. This is a rather conservative estimate of the scattering-limited imaging depth. DSI data averaging will increase the dynamic range and, therefore, improve the imaging depth (up to ≈640 μm with averaging over 100 scans). However, even with the 500 μm imaging depth, the method is useful for certain important medical applications, e.g., diagnostics of skin cancer. Further improvements in detection systems, such as arrays of phase sensitive detectors, will further increase the imaging depth.

FIG. 3 shows 2D-images of a region of the head of *Xenopus Laevis* (African clawed frog) tadpole obtained without averaging and with averaging over 100 Fourier transformed spectra for each one-dimensional scan. The improvement of the image quality with averaging is clearly seen. The images shown in FIG. 3 indicate that DSI with pseudo lock-in detection is a promising technique for in vivo imaging. Compared to OCT, the main drawbacks of this pseudo-lock-in version of DSI are relatively small dynamic range and a low acquisition rate. However, these limitations are not fundamental. Switching to multichannel lock-in detection dramatically improves both the dynamic range and acquisition rate, as next discussed, making DSI competitive to OCT for biomedical imaging.

Using True Lock-in Detection to Obtain DSI Images

The utility of DSI has been shown above with the use of pseudo-lock-in detection. A fast 16-bit CCD imager was binned to provide a read out at 140 Hz (dither frequency was 70 Hz and DSI interferograms were obtained at 70 Hz). However, this was still a high-bandwidth measurement. Each pixel was being read at 250 kHz, providing only a small bandwidth advantage over OCT.

The inherent parallel nature of DSI significantly reduces the bandwidth requirements over OCT, reducing noise and increasing imaging rates. If one employs an array detector with true lock-in detection for each pixel, one can reduce the bandwidth to 30 Hz for video frame rates (in contrast to the bandwidth of an OCT device, which would be ≈1 MHz). However, because of equipment limitations in the earlier testing, in order to test DSI using true lock-in detection, one must give up the inherent parallel data acquisition by using a single element detector. A scanning monochromator was employed together with single channel lock-in detection to fully test DSI. Multichannel phase sensitive detection is, however, preferred.

Figure 9:
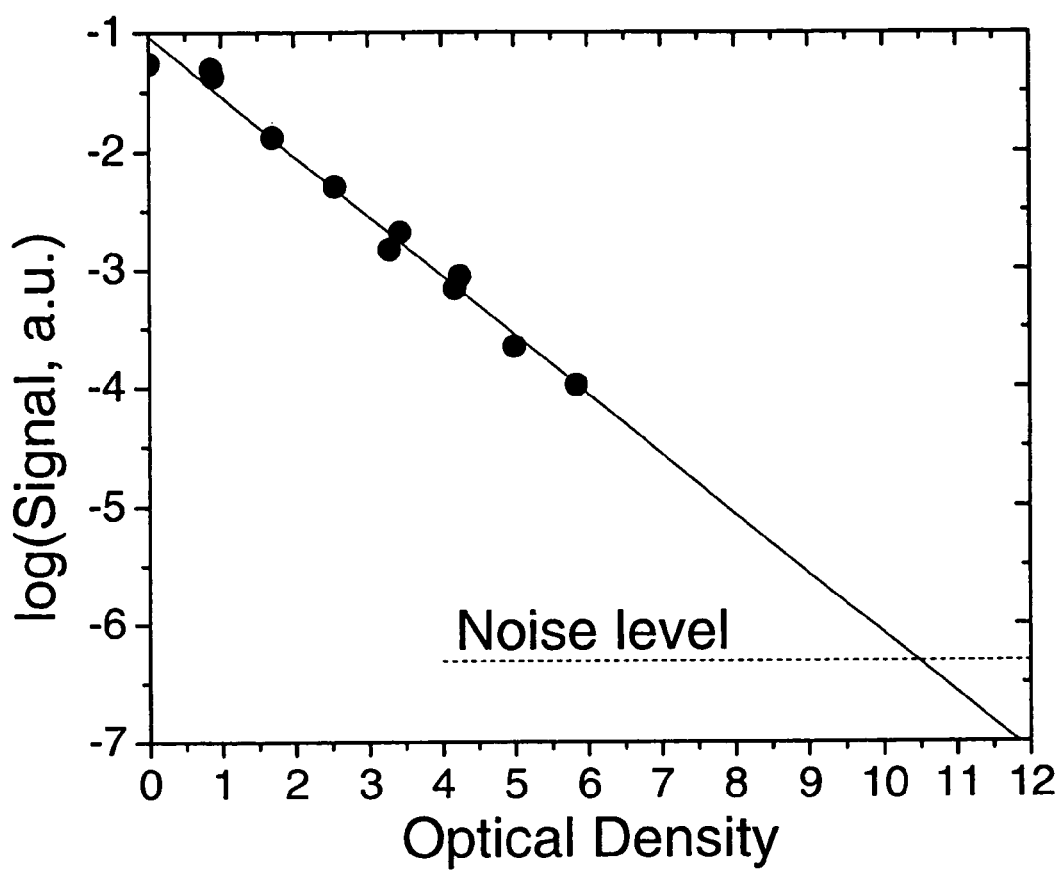
FIG. 9 shows the plot used to determine the dynamic range of the DSI imaging instrument with scanning monochromator/lock-in detection. The plot shows the intensity of the peak corresponding to the image of the mirror with different neutral density (ND) filters inserted in the sample arm of the interferometer. The dashed line indicates the noise level. The light source is a Ti:sapphire laser.

To obtain the DSI images, a sine voltage waveform was applied to the piezo translator of the reference arm mirror to dither it at 1.4 kHz. The wave amplitude was optimized to produce a π phase shift. The differential interferograms were recorded by using the Chromex imaging spectrometer in the scanning mode and lock-in detection of the signal from a photodiode coupled to a laboratory-built transimpedance preamplifier. In these experiments, an aluminum-coated mirror was used as a sample. FIG. 9 shows an example of a differential spectral interferogram and its Fourier transform obtained for a mirror sample mounted in the sample arm 240 µm in front of the reference plane with the laser light source.

Figure 8:
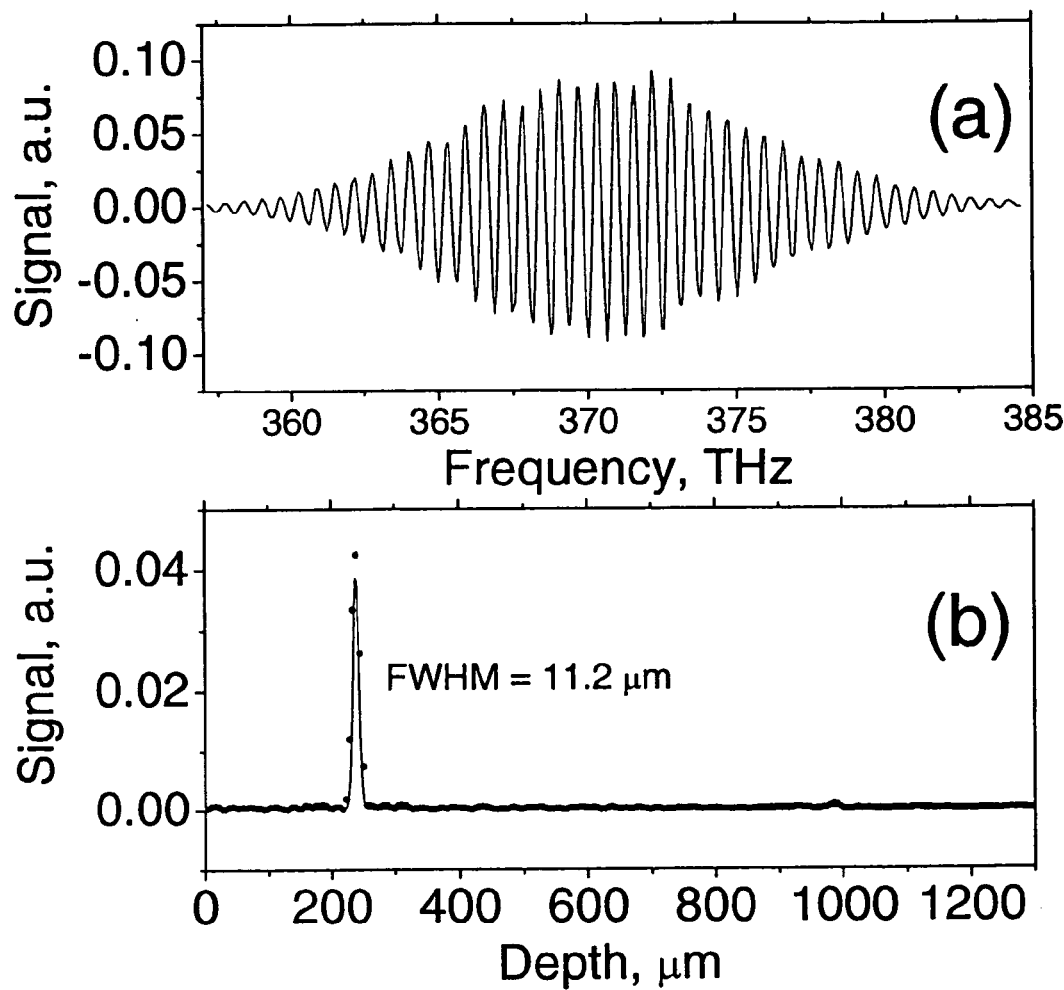
FIG. 8 is a DSI spectrum of a mirror located 240 μm in front of the reference plane obtained with true lock-in detection (a) and its Fourier transform (b). The light source is a passively mode-locked Ti:Sapphire laser. The fitted Gaussian peak width is indicated.

With the scanning monochromator/lock-in detection scheme, one has no limitation on the working spectral window. As seen from FIG. 8(*a*), the whole laser emission spectrum is detected, therefore, narrower peaks can be expected in the measured depth profile. In FIG. 8(*b*), the fitted Gaussian peak width is indicated. With lock-in detection, the peak widths were found to fall within a range of 11.3±1.0 µm, which is close to the Ti:sapphire laser light source bandwidth limit of ~10 µm.

In order to choose an appropriate size of an array detector, a simulation study was performed to determine how the peak width depends on the number of points in the DSI spectrum. The original experimental DSI spectrum (containing 512 points) shown in FIG. 8 was truncated from both ends to leave only 256, 128 or 64 spectral points. Fourier transforms performed on those spectra produced the peaks with FWHM of 11.2 µm, 13.6 µm, 19.4 µm, and 99 µm for the spectra containing 512, 256, 128, and 64 points, respectively. This result shows that an array detector containing as few as 128 elements would provide reasonably good axial resolution.

The dynamic range of a DSI instrument with single-channel lock-in detection was also measured. To determine the dynamic range, the technique described above was employed. As seen in FIG. 9, there is a dramatic improvement in the dynamic range compared to the spectrograph/CCD arrangement (compare FIG. 7). According to FIG. 9, with true lock-in detection, the dynamic range is at least 105 dB. The dynamic range can be even larger, if a more sophisticated (low-noise) signal pre-amplifier is used.

Because of the use of the single-channel detection scheme, the acquisition rate is relatively low. For example, it takes about a half minute to record a one-dimensional profile shown in FIG. 8. With the use of an array detector with true lock-in detection for each pixel, it is possible to improve the image acquisition rate to ~10 Hz for video-rate imaging. For example, with a 128 element array detector, to get a 64×100 image at video rate, the acquisition rate should be one 1D-scan per 1 ms, which is quite reasonable. In the shot-noise limit, for the same effective acquisition rate, DSI with multi-channel lock-in detection would have S/N ratio advantage over OCT of about the square root of the number of channels.

SUMMARY

A novel modification of the Spectral Interferometry (SI) imaging method, Differential Spectral Interferometry (DSI), has been proposed and evaluated. DSI combines the advantages of both Optical Coherence Tomography (OCT) and SI. As with SI, the spectral data are collected in a parallel way, however the data acquisition is performed in an AC mode, allowing low-bandwidth measurements. The results show that DSI provides a dramatic improvement over the SI method in terms of the dynamic range and background suppression. With an instrument it was shown that DSI provides a free-space imaging depth of about 0.5–3 mm (depending on the scattering properties of the sample) with spatial resolution of about 11 µm (which is limited by the bandwidth of the light source). It has been demonstrated that, with DSI, the dynamic range of at least 105 dB is achievable. With the use of an array detector with multi-channel lock-in detection, DSI is competitive with OCT in terms of the dynamic range and image acquisition rate, while maintaining the simplicity of SI. The design of the individually addressed array detector combined with lock-in detection results in an instrument that allows high-quality video rate imaging useful for, among others, applications in medicine, biology, and material science.

Extensions of DSI

By taking the difference signal between a small dither in the reference arm of an interferometer, one directly measures the cosine component of the complex interferogram. By shifting the dither point (nominally by one-fourth the center wavelength), the sine component of the complex interferogram can be measured. The cosine and sine components of the complex interferogram can be thought of as the real and imaginary parts, respectively. Thus, the measurement of the intensity and phase of the entire complex interferogram can be obtained using two dithers and a single lock-in detection scheme allowing for real-time measurement of the complex interferogram. This removes ghosting and double images in the interferogram while allowing for a detection scheme no more complex than required for DSI. One dither has the amplitude required to measure the sine and cosine components while the other dither shifts between sine and cosine component measurement. Other dither waveforms can be used to obtain the complex interferogram as well. However, some dither waveforms are more conducive to lock-in detection than others. Indeed, precalculated waveforms could be designed to optimize the signal recovery and compensate for mechanical response.

To further improve 1/f noise rejection, the magnitude of the Fourier transform of each spectral difference (or spectral set, as in the case of the recovery of the complex interferogram) can be averaged rather than the spectral differences themselves. In the case of the recovery of the complex interferogram, the magnitude of the Fourier transform of each measured complex interferogram can be averaged. Thus, rather than averaging the differences, or equivalently, the real and/or imaginary parts of the interferogram, the Fourier transform of the interferogram (complex or real) is calculated, the magnitude is taken, and the Fourier magnitudes are averaged.

In imaging applications, a wide bandwidth light source is typically used. Obtaining the sine and cosine components using a difference method is absolutely accurate only for a single wavelength of light. However, measuring the sine and cosine components of the complex interferogram using the difference method is typically accurate for imaging requirements even though wide bandwidth sources are used. Adjustments can be made to the dithering waveform to make the measurement more robust for wide bandwidth sources, if required. Also, full digitization of the signal is possible if the waveform is not conducive for measurement with lock-in detection. A digital signal processor can process the digitized signal to obtain the fully corrected interferogram's intensity and phase.

By measuring the complex interferogram in real-time, not only are the stability problems mitigated, but addition and subtraction of the spectra that comprise the complex interferogram measurement efficiently removes background artifacts (as well as other artifacts) and allows for shot-noise limited detection of the complex interferogram.

This method is an extension of the phase retrieval methods outlined by J. Schmidt and K. Creath in their *Applied Optics* paper (Vol. 34, No. 19, pp. 3610–3619). One of the methods of Schmidt and Creath are applied to spectral interferometry by Wojtkowski, et al., supra, but not in the real-time fashion outlined herein.

INDUSTRIAL APPLICABILITY

The invention is further illustrated by the following non-limiting examples.

EXAMPLE 1

The invention can be used to develop a device for determining structural defects in composite materials. The device can be placed on composite and the internal structure of the composite material can be determined.

EXAMPLE 2

The invention can replace optical coherence tomography in any application that OCT can be used.

EXAMPLE 3

The invention can be used to guide surgical instruments.

EXAMPLE 4

If the complete phase of the interferogram can be determined, then the spectral and structural information can be extracted at the same time, within the limits of the uncertainty relationship. Thus, the invention can be used for spectral OCT. This is a great simplification over OCT devices and increases the signal-to-noise ratio over spectral OCT measurements because the inventive technique greatly decreases the detection bandwidth required for measurement.

The examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. An apparatus for differential spectral interferometry, said apparatus comprising:
   an interferometer comprising a light source and an element providing a dithered, continuous relative phase shift between target and reference arms of said interferometer;
   a detector synchronized with said element, said detector synchronously detecting an output from said interferometer and cooperating with one or more other elements of said apparatus to provide spectrally resolved detection; and
   a processor that creates a differential spectral interferogram, said processor operating on data from said detector obtained at relative phase shifts separated by a phase shift difference.

2. The apparatus of claim 1 wherein said light source is mode locked.

3. The apparatus of claim 1 wherein said processor creates said differential spectral interferogram by subtracting spectra that at said relative phase shifts.

4. The apparatus of claim 3 additionally comprising means for performing a Fourier transform of said differential spectral interferogram wherein said phase shift difference is $\pi$.

5. The apparatus of claim 1 additionally comprising means for determining both real and imaginary components of a complex interferogram.

6. The apparatus of claim 5 wherein said processor improves signal-to-noise ratio by averaging a plurality of spectra.

7. The apparatus of claim 1 wherein said element is dithered by a piezo translator.

8. The apparatus of claim 1 wherein said detector is a multi-element detector providing lock-in detection for each of one or more elements of the multi-element detector.

9. The apparatus of claim 1 wherein said phase shift difference is $\pi$.

10. The apparatus of claim 1 wherein said apparatus improves signal-to-noise ratio by averaging a plurality of spectra.

11. The apparatus of claim 1 wherein said apparatus comprises a monochromator.

12. The apparatus of claim 1 wherein said apparatus reduces detection bandwidth to less than the phase modulation frequency.

13. The apparatus of claim 1 wherein said apparatus images biological material.

14. The apparatus of claim 1 wherein said detector employs lock-in detection.

15. An apparatus for differential spectral interferometry, said apparatus comprising:
   an interferometer comprising a light source and an element providing a dithered, continuous relative phase shift between target and reference arms of said interferometer; and
   a multi-element detector providing lock-in detection for two or more elements of said multi-element detector synchronously with said relative phase shift.

16. An apparatus for differential spectral interferometry, said apparatus comprising:
   an interferometer comprising a light source and an element providing a relative phase shift between target and reference arms of the interferometer;
   a multi-element detector providing lock-in detection for two or more elements of said multi-element detector synchronously with said relative phase shift; and a display that displays target characteristics derived from plural differential spectral interferograms of said target derived from plural sets of spectra obtained at relative phase shifts separated by a respective phase shift difference.

17. A method for differential spectral interferometry of a target, the method comprising the steps of:
    providing an interferometer comprising a light source;
    employing an element to provide a dithered, continuous relative phase shift between target and reference arms of the interferometer;
    detecting output from the interferometer synchronously with the dithering; and
    generating a differential spectral interferogram from signals derived by the interferometer at relative phase shifts separated by a phase shift difference.

18. The method of claim 17 wherein the light source is mode locked.

19. The method of claim 17 additionally comprising the step of averaging plural differential spectral interferograms to provide an output characteristic of a position on the target.

20. The method of claim 19 additionally comprising the step of performing a Fourier transform of the resulting differential spectral interferogram.

21. The method of claim 17 additionally comprising the step of determining both real and imaginary components of a complex interferogram.

22. The method of claim 21 additionally comprising the step of improving signal-to-noise ratio by averaging a plurality of spectra.

23. The method of claim 17 wherein the element is coupled to a piezo translator.

24. The method of claim 17 wherein the detector is a multi-element detector and additionally comprising the step of providing lock-in detection for each of two or more elements of the multi-element detector.

25. The method of claim 17 wherein the phase shift is π.

26. The method of claim 17 additionally comprising the step of improving signal-to-noise ratio by averaging a plurality of spectra.

27. The method of claim 17 wherein the output from the interferometer is spectrally resolved.

28. The method of claim 17 wherein the method reduces detection bandwidth to less than the phase modulation frequency.

29. The method of claim 17 additionally comprising the step of displaying characteristics of the target derived from plural differential spectral interferograms.

30. The method of claim 29 wherein the displaying step is performed on biological tissue.

31. A method for differential spectral interferometry, the method comprising the steps of:
    providing an interferometer comprising a light source;
    employing an element to provide a dithered, continuous relative phase shift between target and reference arms of the interferometer;
    providing lock-in detection for each of one or more elements of a multi-element detector, the lock-in detection being synchronous with the relative phase shift; and
    determining a differential spectal interferogram from spectra obtained by the multi-element detector at relative phase shifts separated by a phase shift difference.

32. A method for differential spectral interferometry of a target, the method comprising the steps of:
    providing an interferometer comprising a light source;
    employing an element to provide a dithered, continuous relative phase shift between target and reference arms of the interferometer;
    providing lock-in detection for each of one or more elements of a multi-element detector, the lock-in detection being synchronous with the relative phase shift; and
    displaying target characteristics derived from plural differential spectral interferograms of the target derived from plural sets of spectra obtained at relative phase shifts separated by respective phase shift differences.

* * * * *